United States Patent [19]

Barber et al.

[11] Patent Number: 5,723,769

[45] Date of Patent: Mar. 3, 1998

[54] DIFFUSION CELL

[75] Inventors: Christopher Barber, Darlington; Patrick Hannon, Warwick; Bradley Mark Patterson, Sorrento; Michael George Trefry, Floreat, all of Australia

[73] Assignees: Commonwealth Scientific and Industrial Research Organisation; Greenspan Technology Pty Ltd., both of Australia

[21] Appl. No.: 648,049

[22] PCT Filed: Nov. 18, 1994

[86] PCT No.: PCT/AU94/00714

§ 371 Date: Aug. 28, 1996

§ 102(e) Date: Aug. 28, 1996

[87] PCT Pub. No.: WO95/14223

PCT Pub. Date: May 26, 1995

[30] Foreign Application Priority Data

Nov. 19, 1993 [AU] Australia ................ PM2545
Jun. 7, 1994 [AU] Australia ................ PM6121

[51] Int. Cl.$^6$ ............ G01N 13/00; G01N 27/40; C08G 77/04

[52] U.S. Cl. ........ 73/19.12; 73/64.47; 73/61.73; 73/31.02; 210/640; 422/101

[58] Field of Search ............... 73/19.12, 19.1, 73/64.47, 64.55, 61.73, 31.02; 210/640; 422/101

[56] References Cited

U.S. PATENT DOCUMENTS

| | | | |
|---|---|---|---|
| 2,958,391 | 11/1960 | Derosset | 183/2 |
| 3,300,385 | 1/1967 | Danon | 167/84.5 |
| 3,590,634 | 7/1971 | Pasternak et al. | 73/159 |
| 3,619,986 | 11/1971 | Mormont et al. | 55/158 |
| 3,628,373 | 12/1971 | Gilbert | 73/64.3 |
| 3,877,878 | 4/1975 | Kerfoot et al. | 23/253 TP |
| 4,209,299 | 6/1980 | Carlson | 23/230 R |
| 4,245,495 | 1/1981 | Kakiuchi et al. | 73/643 |
| 4,442,206 | 4/1984 | Michaels et al. | 435/68 |
| 4,541,268 | 9/1985 | Odernheimer | 73/23 |
| 4,603,699 | 8/1986 | Himpens | 128/632 |
| 4,685,463 | 8/1987 | Williams | 128/632 |
| 4,860,577 | 8/1989 | Patterson | 73/64.3 |
| 4,863,696 | 9/1989 | Saydek et al. | 422/101 |
| 4,958,529 | 9/1990 | Vestal | 73/864.81 |
| 5,005,403 | 4/1991 | Steudle et al. | 73/64.3 |
| 5,388,449 | 2/1995 | LeVeen et al. | 73/64.47 |
| 5,428,123 | 6/1995 | Ward et al. | 128/28 |
| 5,498,278 | 3/1996 | Edlund | 96/11 |

FOREIGN PATENT DOCUMENTS

| | | |
|---|---|---|
| 274902 | 1/1990 | United Kingdom. |
| 4114959 | 11/1992 | United Kingdom. |

OTHER PUBLICATIONS

"Sources and Sinks for Dissolved Oxygen in Groundwater in an Unconfined Sand Aquifer," by C. Barber, G. B. Davis and P. Farrington, Western Australia, p. 353. Geochemistry of Gaseous Elements and Compounds, Theophrastus, Publications, SA, Athens, Greece.

C Barber, D Briegel "A method for the In–situ Determination of Dissolved Methane In Groundwater In Shallow Aquifers" Journal of Contaminant Hydrology, 2(1987) 51–60.

C. Barber, G.B. Davies, D. Briegel, J.K. Ward "Factors Controlling The Concentration of Methane and Other Volatiles in Groundwater and Soil–Gas Around a Waste Site", Journal of Contaminant Hydrology, 5(1990) 155–169.

G.B. Davies, C. Barber, D. Briegel, T.R. Power, B.M. Patterson "Sampling Groundwater Quality for Inoganics and Organics: Some Old and New Ideas", Proc. International Drill '92 Conf.

Primary Examiner—Hezron E. Williams
Assistant Examiner—J. David Wiggins
Attorney, Agent, or Firm—Kelly Bauersfeld Lowry & Kelley, LLP

[57] ABSTRACT

A Diffusion cell for use in monitoring levels of gases or volatile organic compounds within bulk media such as ground water, effluent, or air. The diffusion cell is of sealed hollow construction and has a membrane providing an interface between a gas phase contained within the diffusion cell and the bulk media. The membrane is permeable to gas and volatile organic compounds while being relatively impermeable to water (i.e. hydrophobic). The diffusion cell includes a core of porous material to minimize the internal volume within. In use, a sensor is located in close proximity to the core of porous material to minimize the dead volume between the sensor and the diffusion cell. The minimization of the internal and dead volumes allows for decreased response times to fluctuations in levels being measured, lending the diffusion cell to real time monitoring applications.

60 Claims, No Drawings

DIFFUSION CELL

THIS INVENTION relates to a diffusion cell.

This invention has been developed for use in an in-situ monitoring device which is utilised for the environmental and process monitoring, determination and/or measurement of gaseous or volatile products in a bulk medium. For instance, such an in-situ monitoring device is useful for determining the concentration of products such as methane or dissolved oxygen in subsurface ground water, or for determining the levels of products that may be considered to be contaminants of such ground water.

While the present invention is not to be limited only to use with contaminants it is noted that in recent years there has been a growing awareness of the need to develop techniques for the rehabilitation of soils and ground waters that have been contaminated with a range of inorganic and organic materials, such contamination being generally due to improper waste disposal, and spillages and leakages of chemicals from existing or disused industrial sites.

An important aspect of the evolution of these particular rehabilitation techniques has been the development of devices which are capable of sensing contaminants, such as volatile organic compounds and gases (for example, oxygen) in ground waters, industrial effluents and contaminated soils. The volatile organic compounds (VOC's) are often in the form of organic solvents and petroleum fuels, and in particular are substances such as aromatic hydrocarbons, chlorinated ethanes and ethenes. Specifically, volatile organic compounds which are common ground water pollutants are benzene, toluene, ethylbenzene, xylenes (BTEX's), dichloroethane, carbon tetrochloride, chloroform, trichloroethylene (TCE) and tetrachloroethylene (PCE).

Furthermore, it is also known that high concentrations of dissolved methane can occur in some natural ecosystems from leakage of hydrocarbon deposits and also from biogenic sources. The formation of methane by microbial breakdown of organic matter (methanogenesis in anoxic sediments) is common and is known in marine, estuarine and fresh water systems. In deeper subsurface environments such aquifers, methanogenesis can also occur, often being associated with ground water contaminated by waste leachates. Thus, it an be seen that high concentrations of dissolved methane in ground water is a useful indicator of such contamination.

Development of in-situ monitoring devices has also arisen through projects aimed at determining the levels of dissolved oxygen in ground waters, surface waters, affluents and treatment plants. For example, by developing an in-situ monitoring device capable of sensing dissolved oxygen in surface waters, it may be possible to obtain an early warning of the build-up of nuisance algal blooms or waste discharges which deplete dissolved oxygen and affect in-stream ecosystems.

In general, in-situ devices capable of providing real-time data are particularly useful for environmental monitoring, where concentrations and conditions change significantly with time, for example due to diurnal effects or from intermittent contamination. Such devices may be used to monitor and measure the degree of contamination, or may be used to simply attend to constant compliance monitoring of existing facilities which use substances such as organic nonaqueous phase liquids (for example, storage, waste disposal and recovery plants) in order to avoid the contamination problem evident from past experience.

Normally, the techniques used to determine the extent of any contamination would involve the drilling of a network of observation boreholes to allow direct sampling of ground water. However, considerable effort and expense are inevitably involved in such exercises as the techniques for recovering samples are generally extremely labour intensive. Further, and particularly when VOC's are being measured, extensive decontamination procedures are required in order to avoid difficulties associated with cross contamination of samples by VOC's which are easily absorbed from contaminated ground water by flexible (polymer) pump lines. Further still, exposure of such samples to the atmosphere can cause loss of organics by volatilisation, with the subsequent inaccuracies in measuring the concentrations of those organics. In this respect, the levels of contaminants being measured are often of a low order and thus only minor losses or inaccuracies will greatly affect the final determinations.

The present invention provides a diffusion cell for use in an in-situ monitoring device which may be located directly within a variety of different types of bulk media such as subsurface soils, ground waters, surface waters, effluents or atmospheres. A diffusion cell consists of a sealed hollow membrane containing a gas phase connected directly to a gas sensing device. The membrane, which is permeable to gases, such as oxygen, and volatiles, such as VOC's, but is relatively impermeable to water, provides an interface between the gas phase within the cell and the medium external to the cell.

The diffusion cell relies on establishment of an equilibrium between the atmosphere within the open volume and the medium external to the cell (whether the medium is soil, water or gas, with or without a well defined porosity). Thus, and using the example of measuring levels of dissolved oxygen in ground waters, concentration dependent diffusion of dissolved oxygen across the membrane will take place if the partial pressures of the dissolved oxygen in the phases either side of the membrane are unequal. Therefore, if a sealed diffusion cell is placed in a dissolved oxygen rich ground water, then equilibration with respect to the partial pressure of dissolved oxygen in the ground water and in the gas within the open volume of the cell will take place over a period of time.

However, the response of such a diffusion cell to changes in external oxygen concentration is relatively slow compared with the response of a sensor that would be used therewith. While the response time may be adequate for the monitoring of gaseous or volatile products in bulk media such as soil and ground waters, where the concentrations will generally not fluctuate significantly with time, the response time is generally unacceptable for use in surface waters where the concentrations being measured may well fluctuate comparatively rapidly with time.

Accordingly, the present invention has been developed with the aim of reducing the response time to acceptable levels which then allows the diffusion cell of the invention to be utilised in an in-situ real-time monitoring device which may be used to measure the level of gaseous or volatile products in both ground waters and soils, but also in surface waters, and in any situation where a faster response time is required.

The present invention is characterized by a diffusion cell which comprises a hollow polymer membrane having therewithin a core of porous material. Thus, the present invention provides a diffusion cell for use in an in-situ monitoring device for location directly within different types of bulk media, the diffusion cell comprising a sealed hollow membrane capable of containing a gas phase, the membrane being capable of being connected in fluid communication with a gas sensing device, the membrane providing a interface, in use, between the gas phase therewithin and the bulk medium externally thereof, wherein the membrane includes therewith a core of porous material. The core is preferably reasonably rigid so as to provide the diffusion cell with a degree of rigidity and strength. In a preferred form of the invention, the polymer membrane is a length of small diameter, thin walled, hollow fibre polymer tubing and the core of porous material is an elongate rod of a size suitable to fit within the tubing.

The polymer membrane may be any time of polymeric material as necessary. In this respect, volatiles and gases readily diffuse through most polymeric materials, rates of diffusion being least for less flexible polymers like teflon, and greatest for more flexible polymers such as silicone (poly(dimethyl)siloxane).

The porous material is preferably provided in the form of a sintered rod such as a sintered copper nickel rod.

It is expected that different polymeric materials will be better suited in some uses than in others, and it is also expected that the diameter of the polymeric tubing, the size of the porous core, and the porosity of the porous core, will all also need to be selected as appropriate by methods of trial and experiment when different uses are required for the diffusion cell. In this respect, while the following details have been described in relation to the use of the diffusion cell in sensing dissolved oxygen in ground waters and surface waters, and thus the parameters described are suitable for that use, it is likely that these parameters will be altered in situations where the diffusion cell is required to sense the presence and levels of gases and volatiles whether they be in ground waters, surface waters, or contaminated soils, effluent or atmospheres.

As indicated above, the diffusion cell of the present invention has been developed for use in an in-situ monitoring device. The device preferably comprises a body having located therewithin the instrumentation necessary for the sensing, reading and determining of the presence of the product to be measured. Thus, the body may include therewithin a sensor of a known type and a date processor/logger for capturing the relevant information.

In particular, the body necessarily includes electronic circuitry for amplification or modulation of sensor output signal. In this respect, the sensor may be electronically connected to a signal conditioning circuit board capable of converting the voltage from the diffusion cell to a current proportional to oxygen concentration. The circuit may preferably provide for two optional configurations; firstly, an output which is temperature adjusted to represent product as parts per million; and secondly, an output which is not temperature adjusted and which is adjusted to represent percent saturation of dissolved substance in aqueous solution; or in the case of measurement taking place in an atmosphere, percent saturation of substance in the atmosphere. Further circuitry may provide for an optional signal processing capability that converts the amplified sensor output signal into an enhanced estimate of product concentration.

The body may be provided with or without its own power supply such that the device may be used with or without the need for the use of an umbilical cord. Of course, in most instances there would be a need for the umbilical cord to include a power line and also a line for transferring data from the device to an externally located analysing system. The diffusion cell may then be secured to the body of the device to be in close proximity to the sensor.

With regard to the location of the diffusion cell, it is preferred that the core of porous material be located as closely as possible to the sensor in order to reduce to a minimum any dead volume between the core and the sensor. In this respect, it has been found that by reducing this dead volume to a minimum, the response time of the device is also minimised. Specific examples of possible parameters for a diffusion cell will now be described in relation to the following examples. In this respect, it will be noted that these examples relate to the use of the diffusion cell to determine levels of dissolved oxygen in surface waters. It will also be noted that the tests described in the following examples were carried out on the preferred diffusion cell geometry (namely, using hollow fibre tubing). However, the present invention is not to be limited to use only in these circumstances.

Different configurations (length, diameter, wall thickness) of polymer membrane for attachment to oxygen sensors were tested under well-mixed gaseous and aqueous oxygenated and deoxygenated conditions. Silicone tubing was used as the preferred polymer membrane.

Response times were estimated based on the time for a 90% change in the oxygen reading from the oxygen sensor in response to a step increase or decrease external to the cell/sensor device. Also tested were the effects of reducing the open volume or "dead volume" at the connection point between the diffusion cell and the oxygen sensor and the effects of the insertion of the core of porous material, in the form of sintered rods, into the diffusion cells to thus reduce the internal volume of the diffusion cell.

After laboratory testing it was apparent that minimum response times were achieved for a reduced "dead volume" and for smaller diameter tubing, and for a sintered rod inserted within the larger diameter tubing. Response times for these conditions were 32 to 48 minutes for a step change in dissolved oxygen and 22 to 28 minutes for gaseous oxygen. Theoretical modelling suggested that response times could be below 10 minutes for a zero "dead volume" and for smaller diameter tubing.

Results from studies with some diffusion cells (having parameters of 3.18 mm outside diameter, 1.98 mm internal diameter, and length of 20 cm) suggested that the response time of a gas within a diffusion cell was approximately 100 minutes for a 2 to 3 mg $L^{-1}$ change in dissolved oxygen of water external to the cell. This was without an inner core of porous material.

Further work was undertaken in an attempt to reduce the response time by altering the dimensions of the diffusion cell and to investigate the apparent effect of tubing length. A range of different size silicone tubing was tested to determine the dimensions that would reduce the response time of the diffusion cell/sensor.

Diffusion cells were attached to oxygen sensors using a nylon SWAGELOK (registered trade mark) fitting. A stainless steel reducer was used with the SWAGELOK fitting for smaller diameter tubing (1.00 and 1.02 mm internal diameter). Tests were carried out in duplicate. Response times were determined for both decreasing and increasing oxygen partial pressure as the time to achieve a 90% change, and average values for each duplicate are reported in Tables 1 and 2.

Initial tests were performed under gaseous conditions (air=oxygenated and nitrogen=deoxygenated). Sensors without diffusion cells were used as controls. Diffusion cell/sensors were set up within an air tight container with an inlet for compressed air or compressed nitrogen and an outlet for effluent gas. The container was flushed with air until a stable oxygen reading occurred then flushed with nitrogen. The results for gaseous conditions are given in Table 1.

For tests under aqueous conditions, the airtight container was filled with water and deoxygenated by the addition of sodium sulfite, and maintained by the bubbling of nitrogen through the water. Oxygenated conditions (about 8.7 mg L$^{-1}$) were achieved by replacing the deoxygenated water with oxygenated water that had been previously aerated. Oxygenated conditions were maintained by continued air bubbling through the water. The results for aqueous conditions are given in Table 2.

The effect of dead volume (volume of gas within the sensor and SWAGELOK fitting not in contact with the silicon tubing and thus not permeable to oxygen diffusion( on response times were also evaluated. Test were carried out using cell/sensors with dead volumes of approximately 200 microliters and 50 microliters. The dead volume was decreased by reducing the internal volume of the SWAGELOK fitting with teflon tubing and reducing the volume between the sensor and SWAGELOK fitting with a rubber o-ring. This also gave a better air tight seal between the sensor and SWAGELOK fitting.

Under gaseous conditions with a dead volume of about 200 m microliters, the effect of tubing length was shown to significantly alter response times (Table 1) for the larger diameter tubing (3.18 mm od). In particular, the response time reduced from 100 to 140 minutes for the 5 cm length (cell type A—see Table 3) to 40 to 45 minutes for the 80 cm length (cell type C). The tubing length effect was not as significant for the smaller diameter tubing (1.5 mm cd, cell types F and G). In fact, response time reduced only marginally from 90 to 135 minutes for the 20 cm length (cell type F) to 85 to 110 minutes for the 80 cm length (cell type G).

Thus, tubing beyond a critical length would appear to have the same response time because of the time for gases to diffuse along the length of the tubing into the dead volume. The effect of the dead volume is more pronounced with shorter tubelengths, increasing the response time.

With a reduction in dead volume to about 50 microliters, all response times were reduced. In general, cell types with small gas volumes (cell type A, E and F) show greater reductions in response times (Table 1). Further, the effect of tubing length for thick tubing (cell type A, B and C) was still significant for cell type A. Cell type B and C showed no significant difference in response time. Again, no significant differences in response times were observed in the smaller diameter tubing (cell type F and G).

Under gaseous conditions with a dead volume of about 200 microliters, the effect of wall thickness was only minimial. Comparison of diffusion cells of similar internal diameter but different wall thicknesses (cell types E and F) show only minor differences (Table 1). With a smaller dead volume (about 50 microliters), the cell type with the smaller wall thickness (cell type F) has a slightly reduced response time (Table 1). However, it should be appreciated that results for tubes of similar dimensions were sometimes different because tube dimensions (thickness) often varied by as much as ±40%.

The effect of increased surface area to volume ratio was compared in two tests. In one test the surface area to volume ratio was increased by the addition of a wire spacer to the diffusion cell. Comparison of the response time of a cell with a wire spacer (cell type D) to one without (cell type B) shows no significant differences. In the second test a larger surface area to volume ratio was established with a 30 micron sintered copper nickel rod (with a porosity of about 24%) inserted within the diffusion cell (cell type H). Large diameter tubing (3.18 mm od, 1.98 mm id) was used so as not to excessively change the dimensions of the tubing over the sintered rod. Thus, results could be compared to tubing without the sintered rod (cell type B). The use of the sintered rod reduced the response time by 20 to 24% in the gas phase and 29 to 45% in the aqueous phase (comparison of cell type H to B). Results with the sintered rod (cell type H) showed more variability between duplicates than other cell types, indicating the porosity of the sintered rods may not be consistent.

Tests were also conducted with sintered rods having a pore size in the range of 10 microns to 100 microns, with the 10 micron rods proving to be most preferred.

The quantity of gas within the sensor and fitting (dead volume) appears to affect response times. The tubing length effect as described is related to the presence of the dead volume. However, with a zero dead volume and with no loss of oxygen from the gas phase, modelling indicates there should be no length effect. For best results the total volume within the silicone tubing and fitting (including dead volume) needs to be small, and fastest response times were obtained with cell types with small dead volumes (about 50 microliters) and thin wall thicknesses (cell type F and G, about 25 minutes in air and about 40 minutes in water) or larger surface area to volume ratios (cell type H, about 24 minutes in air and about 36 minutes in water). Quicker response times could be achieved with a combination of further reduction in (i) dead volume, (ii) wall thickness and (iii) internal volume.

Simple model evaluation provides a theoretical basis for interpretation of these effects. From this it is apparent that within the diffusion cell, the number of molecules of oxygen required to diffuse through the polymer to reach a new equilibrium when concentration outside the cell changes, will be dependent on the internal volume of gas in the cell. Thus, the lower the internal gas volume, the lower the number of molecules required to establish equilibrium and the lower the overall response time for a given cell surface area. Thus, increasing the surface area to internal volume ratio assists in reducing response time.

Thus, it can be seen that the introduction of a core of porous material to the diffusion cell significantly reduces the response time of an in-situ monitoring device utilising the diffusion cell of the present invention. Further, the reduction of the dead volume in the in-situ monitoring device also provides a beneficial advantage in reducing the response time of the device, although it must be appreciated that the reduction of the dead volume is merely a highly preferred feature of the in-situ monitoring device which utilises the diffusion cell of the invention.

However, even with these improvements, the response times of the diffusion cell may still often be of the order of twenty minutes. Such responses are acceptable in situations where dissolved oxygen concentrations vary slowly over periods of hours, but may be unacceptable where concentrations vary more quickly. To reduce the device response time further a signal processing algorithm was developed (this algorithm will be referred to as the "estimation algorithm"). The estimation algorithm takes advantage of predictability in the response of the diffusion cell to well mixed media to estimate equilibrium concentrations well before equilibrium is actually reached.

This estimation procedure is preferably implemented as follows. A calibration process is performed on the relaxation of the device to equilibrium with a well mixed medium of known dissolved oxygen concentrations. Measurements of the output of the device logger during relaxation are used to fit the device response rate parameter, $\beta$, according to the following characteristic equation:

$$C(t) = C_{eq} + (C_0 - C_{eq})\exp(-\beta t) \quad (1)$$

Here C(t) represents the device output at time t, $C_0$ represents the initial concentration reading of the device and $C_{eq}$ represents the actual concentration of the sampled medium (the quantity of interest). This equation models the response of a diffusive sensor to a well mixed medium. Whilst the assumption of well mixed media is not valid for all field applications, modelling studies indicate that equation (1) is often as good a fit to experiment as equations given by more sophisticated mixing formulations. Furthermore the minor approximations inherent in this assumption are outweighed by its broad utility. Theoretical studies also show that the response rate is independent of $C_0$ and $C_{eq}$ and incorporates geometrical information of the device. Hence the calibrated response rate $\beta_{cal}$ may vary from device to device and must be measured for each device before use and stored in non-volatile electronic memory.

During actual use, $\beta_{cal}$ is combined with successive outputs, $C(t_{i-1})$ and $C(t_i)$, from the sensor and the time separation $\Delta t = t_i - t_{i-1}$ to estimate the final equilibrium concentration value that would be reached after infinite relaxation time:

$$C_{eq}^{estimate}(t_i) = \frac{(C(t_i) - C(t_{i-1})\exp(-\beta_{cal}\Delta t))}{(1 - \exp(-\beta_{cal}\Delta t))} \quad (2)$$

This estimation algorithm is derived by applying a simple two-point difference formula for the time derivative of equation (1). Tests with laboratory data confirm that the algorithm provides estimates of concentration that are significantly more accurate than the simple unprocessed sensor output. Theoretical modelling suggests that, for the magnitude of errors commonly present in the sensor output, this estimation algorithm is quite stable even if the value of the calibrated response rate $\beta_{cal}$ is inaccurate by up to 10%. Further reduction of errors in the estimation procedure may be gained by combining several previous output measurements at once. This averaging process may be formalised by the following weighting procedure:

$$E(t_i) = \Omega^{-1}\left(\omega_i \frac{(C(t_i) - C(t_{i-1})\exp(-\beta_{cal}\Delta t))}{(1 - \exp(-\beta_{cal}\Delta t))} + \sum_{j=2}^{N}\omega_j G_{i-j+1}\right) \quad (3)$$

where the overall normaliser $\Omega$ is given by:

$$\Omega = \sum_{j=1}^{N}\omega_j$$

The above enhancement process for the (averaged) estimated value $E(t_i)$ contains the runlength parameter, N. This integer parameter determines the number of previous signals to combine in the weighted averaging process. Setting $N=\omega_1=1$ recovers the standard algorithm in equation (2). The weighting parameters $\Omega_j$ form a set of length N and determine the relative weights of the N previous generalised measurements, $G_i$, in the averaging process. The generalised measurement quantity, $G_i$, may take several forms, e.g. $G_i=C(t_i)$ averages the new estimate with the previous unprocessed measurements, while $G_i=E(t_i)$ averages the new estimate with the previous estimates. Higher values of N in equation (3) reduce errors in the concentration estimates $E(t_i)$ by averaging over more previous readings. There is a trade-off situation in optimising N and the weights $\omega_j$ with their optimal values also having a minor dependence on the behaviour of the concentration signal being monitored. Any explicit functional form may be employed for the weights, although a common and useful choice is that of $\omega_j = j^{-1}$. This choice, together with N=3, can reduce average deviations in the concentration estimates by up to 5%, although using N>1 tends to reduce the sensitivity of the algorithm to rapid changes in dissolved oxygen concentration.

In summary, this signal processing algorithm can be used to gain rapid and accurate estimates of dissolved oxygen concentrations. The estimation algorithm utilises the mathematical characteristics of the diffusion cell to predict equilibrium concentrations from as little as two successive sensor measurements, allowing the predictions to correlate dynamically with the actual medium concentrations. It can be seen that the signal processing algorithm is simple enough to be incorporated into the normal electronic data processing/logging unit on the diffusion cell, yielding an enhanced means of determining dissolved oxygen concentrations.

It can also be seen that the diffusion cell of the present invention is capable of being used with in-situ monitoring devices that are required for sensing a variety of gases and volatiles in a variety of bulk media. Indeed, with variations to the various parameters of the diffusion cell, and with necessary adaptations being made to the instrumentation within the body of the in-situ monitoring device, it is envisaged that the diffusion cell of this invention will be useful for applications both above and below ground, and in ground waters, effluents, atmospheres and surface waters for monitoring, determining and measuring the concentrations of a variety of gaseous and volatile products.

Finally, it will be understood that there may be other variations and modifications that may be made to the configurations described herein that are also within the scope of the present invention.

TABLE 1

| Diffusion Cell Type | Gas response time to 90% change in oxygen partial pressure | | | | | |
|---|---|---|---|---|---|---|
| | dead volume 200 ul | | dead volume 50 ul | | reduction in response time | |
| | decreasing (min) | increasing (min) | decreasing (min) | increasing (min) | decreasing (%) | increasing (%) |
| A | 140 | 100 | 38 | 35 | 73 | 65 |
| B | 70 | 70 | 29 | 31 | 59 | 56 |
| C | 40 | 45 | 30 | 31 | 25 | 31 |
| D | 70 | 65 | 25 | 28 | 64 | 57 |
| E | 95 | 125 | 29 | 32 | 69 | 74 |
| F | 90 | 135 | 23 | 25 | 74 | 81 |
| G | 85 | 110 | 22 | 25 | 74 | 77 |
| H | — | — | 23 | 25 | — | — |

TABLE 2

Liquid response time to 90% change in oxygen partial pressure

| Diffusion Cell Type | dead volume 200 ul decreasing (min) | dead volume 200 ul increasing (min) | dead volume 50 ul decreasing (min) | dead volume 50 ul increasing (min) | reduction in response time decreasing (%) | reduction in response time increasing (%) |
|---|---|---|---|---|---|---|
| A | 220 | 260 | 64 | 66 | 71 | 75 |
| B | 125 | 170 | 58 | 58 | 54 | 66 |
| C | 85 | 105 | 60 | 68 | 29 | 35 |
| D | 115 | 160 | 45 | 46 | 61 | 71 |
| E | 240 | 275 | 44 | 48 | 82 | 83 |
| F | 230 | 260 | 38 | 46 | 83 | 82 |
| G | 170 | 215 | 36 | 44 | 79 | 80 |
| H | — | — | 32 | 41 | — | — |

TABLE 3

Dimensions of diffusion cell types

| Diffusion Cell Type | Tubing I.d. (mm) | Tubing o.d. (mm) | Wall Thickness (mm) | Length of Tubing (cm) | Volume Inside Tubing (ml) | Volume of Wire or Scintered Rod° (ml) | Gas Volume Inside Tubing Volume (ml) | I.d. Suface Area (cm sq) | o.d. Surface Area (cm sq) | I.d. Surface Area/vol. (cm sq/ml) | o.d. Surface Area/vol. (cm sq/ml) | Volume of Silicone (ml) |
|---|---|---|---|---|---|---|---|---|---|---|---|---|
| A | 1.98 | 3.18 | 0.60 | 5 | 0.15 | 0.00 | 0.15 | 3.11 | 5.0 | 20 | 32 | 0.24 |
| B | 1.98 | 3.18 | 0.60 | 20 | 0.62 | 0.00 | 0.62 | 12.45 | 20.0 | 20 | 32 | 0.97 |
| C | 1.98 | 3.18 | 0.60 | 80 | 2.46 | 0.00 | 2.46 | 49.78 | 80.0 | 20 | 32 | 3.89 |
| D | 1.98 | 3.18 | 0.60 | 20 | 0.62 | 0.10 | 0.51 | 12.45 | 20.0 | 24 | 39 | 0.97 |
| E | 1.02 | 2.16 | 0.57 | 20 | 0.16 | 0.00 | 0.16 | 6.41 | 13.6 | 39 | 83 | 0.57 |
| F | 1.00 | 1.50 | 0.25 | 20 | 0.16 | 0.00 | 0.16 | 6.29 | 9.4 | 40 | 60 | 0.20 |
| G | 1.00 | 1.50 | 0.26 | 80 | 0.63 | 0.00 | 0.63 | 25.14 | 37.7 | 40 | 60 | 0.79 |
| H | 3.30 | 4.10 | 0.40 | 16 | 1.37 | 0.98 | 0.39 | 16.59 | 20.6 | 43 | 53 | 0.74 |

We claim:

1. A gas or volatile organic compound in-situ monitoring device diffusion cell for location directly within different types of bulk media, the diffusion cell being of sealed hollow configuration and comprising a membrane capable of containing a gas phase within said diffusion cell on a first side of said membrane, the membrane being permeable to gasses and volatile organic compounds and relatively impermeable to water, the membrane providing an interface, in use, between the gas phase therewithin and the bulk medium externally thereof on a second side of said membrane, wherein the diffusion cell includes therewithin on said first side a core of porous material to minimize the internal volume therewithin, and wherein the diffusion cell is capable of being connected in fluid communication with a gas or volatile organic compound sensitive sensor to measure the level of gas or volatile organic compounds, the core of porous material and the sensor being, in use, located in close proximity to reduce the dead volume between the diffusion cell and the sensor.

2. A diffusion cell according to claim 1 wherein the core is an elongate rod and is reasonably rigid so as to provide the diffusion cell with a degree of rigidity and strength.

3. A diffusion cell according to claim 2 wherein the core is a sintered rod.

4. A diffusion cell according to claim 3 wherein the sintered rod is a sintered copper nickel alloy rod.

5. A diffusion cell according to claim 1 wherein the membrane is a length of small diameter, thin walled, hollow fiber polymer tube.

6. A diffusion cell according to claim 1 wherein the core has a pore size less than about 100 micron.

7. A diffusion cell according to claim 1 wherein the pore size of the core is about 10 micron.

8. A diffusion cell according to claim 1 wherein the membrane has a wall thickness less than about 0.6 mm.

9. A diffusion cell according to claim 1 wherein the membrane has a well thickness of about 0.25 mm.

10. A diffusion cell according to claim 1 wherein the ratio of the internal surface area of the membrane to the volume within the membrane is greater than about 20 cm$^2$ ml.

11. A diffusion cell according to claim 10 wherein the ratio is greater than about 40 cm$^2$ ml$^{-1}$.

12. A device according to claim 1, wherein the dead volume is less than about 200 microliters.

13. A device according to claim 1 wherein the dead volume is less than about 100 microliters.

14. A device according to claim 1 wherein the dead volume is less than about 50 microliters.

15. A diffusion cell for use in an in-situ monitoring device for location directly within different types of bulk media; the diffusion cell comprising a sealed hollow membrane capable of containing a gas phase, the membrane being capable of being connected in fluid communication with a gas sensing device, the membrane providing an interface, in use, between the gas phase therewithin and the bulk medium externally thereof, wherein the membrane includes therewithin a core of porous material, and wherein the core is a sintered rod, the membrane is a length of small diameter, thin walled, hollow fiber polymer tube, the core has a pore size less than about 100 micron, the membrane has a wall thickness less than about 0.6 mm, and wherein the ratio of the internal surface area of the membrane to the volume within the membrane is greater than about 20 cm$^2$ ml$^{-1}$.

16. An in-situ monitoring device according to claim 15 for location directly within different types of bulk media for measuring the levels of gaseous or volatile products therein, the device comprising instrumentation necessary for sensing, reading and determining the presence of the product to be measured, the instrument including a sensor connected in fluid communication to the diffusion cell of claim 27, and a data processing means.

17. A device according to claim 15 wherein the connection of the sensor to the diffusion cell is configured so as to minimize dead volume therewithin, wherein the connection comprises a connecting means connecting the diffusion cell to the sensor, connected so as to reduce the internal volume of the connecting means and so as to reduce the volume between the connecting means and the sensor, and wherein the dead volume is less than about 50 microliters.

18. A device according to claim 16 wherein the data processing means includes means for amplification or modulation of sensor output signal, and wherein the data processing means is capable of providing different outputs; firstly an output which is temperature adjusted to represent product as parts per million; and secondly, an output which is not temperature adjusted and which is adjusted to represent percent saturation of said gaseous or volatile products in said bulk media.

19. A gas or volatile organic compound in-situ monitoring device diffusion cell for location directly within different types of bulk media, the diffusion cell being of sealed hollow configuration and comprising a membrane capable of containing a gas phase within said diffusion cell on a first side of said membrane, the membrane being permeable to gasses and volatile organic compounds and relatively impermeable to water, the membrane providing an interface, in use, between the gas phase therewithin and the bulk medium externally thereof on a second side of said membrane, wherein the diffusion cell includes therewithin on said first side a core of porous material to minimize the internal volume therewithin, and wherein the diffusion cell includes a gas or volatile organic compound sensitive sensor connected in fluid communication therewith to measure the level of gas or volatile organic compounds, the core of porous material and the sensor being located in close proximity to reduce the dead volume there between.

20. A diffusion cell according to claim 19 wherein the core is an elongate rod and is reasonably rigid so as to provide the diffusion cell with a degree of rigidity and strength.

21. A diffusion cell according to claim 20 wherein the core is a sintered rod.

22. A diffusion cell according to claim 21 wherein the sintered rod is a sintered copper nickel alloy rod.

23. A diffusion cell according to claim 19 wherein the membrane is a length of small diameter, thin walled, hollow fiber polymer tube.

24. A diffusion cell according to claim 19 wherein the core has a pore size less than about 100 micron.

25. A diffusion cell according to claim 19 wherein the pore size of the core is about 10 micron.

26. A diffusion cell according to claim 19 wherein the membrane has a wall thickness less than about 0.6 mm.

27. A diffusion cell according to claim 19 wherein the membrane has a wall thickness of about 0.25 mm.

28. A diffusion cell according to claim 19 wherein the ratio of the internal surface area of the membrane to the internal volume within the membrane is greater than about 20 $cm^2 \cdot ml^{-1}$.

29. A diffusion cell according to claim 28 wherein the ratio is greater than about 40 $cm^2 \cdot ml^{-1}$.

30. A device according to claim 19 wherein the dead volume is less than about 200 microliters.

31. A device according to claim 19 wherein the dead volume is less than about 100 microliters.

32. A device according to claim 19 wherein the dead volume is less than about 50 microliters.

33. An in-situ monitoring device for location directly within different types of bulk media for measuring the levels of gaseous or volatile products therein, the device comprising instrumentation necessary for sensing, regarding and determining the presence of the product to be measured, the instrumentation including a gas or volatile organic compound sensitive sensor connected in fluid communication to the diffusion cell of claim 31, and a data processing means.

34. A device according to claim 33 wherein the data processing means is capable of providing different outputs; firstly an output which is temperature adjusted to represent product as parts per million; and secondly, an output which is not temperature adjusted and which is adjusted to represent percent saturation of dissolved gas or volatile organic compound in solution in the bulk medium.

35. A device according to claim 33 wherein the data processing means utilizes a signal processing algorithm in the form of the estimation algorithm described herein.

36. A gas or volatile organic compound in-situ monitoring device diffusion cell for location directly within different types of bulk media, the diffusion cell being of sealed hollow configuration and comprising a membrane capable of containing a gas phase within said diffusion cell on a first side of said membrane, the membrane being permeable to gasses and volatile organic compounds and relatively impermeable to water, the membrane providing an interface, in use, between the gas phase therewithin and the bulk medium externally thereof on a second side of said membrane, wherein the diffusion cell includes therewithin on said first side a core of porous material to minimize the internal volume therewithin, and wherein the diffusion cell includes a gas or volatile organic compound sensitive sensor connected in fluid communication therewith to measure the level of gas or volatile organic compounds, the core of porous material and the sensor being located in close proximity to reduce the dead volume there between, and wherein the dead volume is less than about 200 microliters.

37. A device according to claim 36 wherein the dead volume is less than about 100 microliters.

38. A device according to claim 36 wherein the dead volume is less than about 50 microliters.

39. A diffusion cell according to claim 36 wherein the core is an elongate rod and is reasonable rigid so as to provide the diffusion cell with a degree of rigidity and strength.

40. A diffusion cell according to claim 39 wherein the core is a sintered rod.

41. A diffusion cell according to claim 40 wherein the sintered rod is a sintered copper nickel alloy rod.

42. A diffusion cell according to claim 36 wherein the membrane is a length of small diameter, thin walled, hollow fiber polymer tube.

43. A diffusion cell according to claim 36 wherein the core has a pore size less than about 100 micron.

44. A diffusion cell according to claim 36 wherein the pore size of the core is about 10 micron.

45. A diffusion cell according to claim 36 wherein the membrane has a wall thickness less than about 0.6 mm.

46. A diffusion cell according to claim 36 wherein the membrane has a wall thickness of about 0.25 mm.

47. A diffusion cell according to claim 36 wherein the ratio of the internal surface area of the membrane to the internal volume within the membrane is greater than about 20 $cm^2 \cdot ml^{-1}$.

48. A diffusion cell according to claim 47 wherein the ratio is greater than about 40 $cm^2 \cdot l^{-1}$.

49. A gas or volatile organic compound in-situ monitoring device diffusion cell for location directly within different types of bulk media, the diffusion cell being of sealed hollow configuration and comprising a membrane capable of containing a gas phase within said diffusion cell on a first side of said membrane, the membrane being permeable to gasses and volatile organic compounds and relatively impermeable to water, the membrane providing an interface, in use, between the gas phase therewithin and the bulk medium externally thereof on a second side of said membrane, wherein the diffusion cell includes therewithin on said first side a core of porous material to minimize the internal volume therewithin, and wherein the diffusion cell includes a gas or volatile organic compound sensitive sensor connected in fluid communication therewith to measure the level of gas or volatile organic compounds, the core of porous material and the sensor being located in close proximity to reduce the dead volume there between, and wherein the ratio of the internal surface area of the membrane to the volume within the membrane is greater than about 20 $cm^2 \cdot ml^{-1}$.

50. A diffusion cell according to claim 49 wherein the ratio is greater than about 40 $cm^2 \cdot ml^{-1}$.

51. A diffusion cell according to claim 49 wherein the core is an elongate rod and is reasonably rigid so as to provide the diffusion cell with a degree of rigidity and strength.

52. A diffusion cell according to claim 51 wherein the core is a sintered rod.

53. A diffusion cell according to claim 52 wherein the sintered rod is a sintered copper nickel alloy rod.

54. A diffusion cell according to claim 49 wherein the membrane is a length of small diameter, thin walled, hollow fiber polymer tube.

55. A diffusion cell according to claim 49 wherein the core has a pore size less than about 100 micron.

56. A diffusion cell according to claim 49 wherein the pore size of the core is about 10 micron.

57. A diffusion cell according to claim 49 wherein the membrane has a wall thickness less than about 0.6 mm.

58. A diffusion cell according to claim 49 wherein the membrane has a wall thickness of about 0.25 mm.

59. A device according to claim 49 wherein the dead volume is less than about 100 microliters.

60. A device according to claim 49 wherein the dead volume is less than about 50 microliters.

* * * * *